(12) United States Patent
Macinnis (10) Patent No.: US 10,912,641 B2
(45) Date of Patent: Feb. 9, 2021

(54) OPHTHALMIC DEVICES AND METHODS

(71) Applicant: Brent Macinnis, Ottawa (CA)

(72) Inventor: Brent Macinnis, Ottawa (CA)

( * ) Notice: Subject to any disclaimer, the term of this patent is extended or adjusted under 35 U.S.C. 154(b) by 427 days.

(21) Appl. No.: 15/845,609

(22) Filed: Dec. 18, 2017

(65) Prior Publication Data

US 2019/0183635 A1     Jun. 20, 2019

(51) Int. Cl.
| | |
|---|---|
| *A61F 2/16* | (2006.01) |
| *G02B 1/00* | (2006.01) |
| *G02C 7/04* | (2006.01) |
| G02C 7/10 | (2006.01) |
| G02B 5/22 | (2006.01) |
| G02B 1/04 | (2006.01) |

(52) U.S. Cl.
CPC ............ *A61F 2/1613* (2013.01); *G02B 1/002* (2013.01); *G02C 7/049* (2013.01); *A61F 2/1651* (2015.04); *A61F 2002/1683* (2013.01); *G02B 1/043* (2013.01); *G02B 5/22* (2013.01); *G02C 7/10* (2013.01)

(58) Field of Classification Search
CPC ....... G02B 1/002; G02B 1/118; A61F 2/1613; A61F 2/1648; A61F 2/1451
See application file for complete search history.

(56) References Cited

U.S. PATENT DOCUMENTS

| | | | |
|---|---|---|---|
| 9,151,891 B2 | 10/2015 | Ma et al. | |
| 9,482,796 B2 | 11/2016 | Arbabi et al. | |
| 9,658,469 B2 | 5/2017 | Pugh et al. | |
| 9,664,817 B1 | 5/2017 | Di Falco | |
| 9,775,932 B2 | 10/2017 | Desai et al. | |
| 2002/0159160 A1 | 10/2002 | Kayanoki et al. | |
| 2012/0259411 A1* | 10/2012 | Hong | A61F 2/16 623/6.56 |
| 2017/0082263 A1 | 3/2017 | Byrnes et al. | |

(Continued)

FOREIGN PATENT DOCUMENTS

| | | |
|---|---|---|
| CA | 2831640 | 10/2012 |
| CA | 2846645 | 9/2014 |
| WO | 2017176921 | 10/2017 |

OTHER PUBLICATIONS

Search Report and Written Opinion dated Aug. 13, 2018 for International application No. PCT/CA2017/051529, which is related to U.S. Appl. No. 15/845,609.

(Continued)

*Primary Examiner* — William H Matthews
(74) *Attorney, Agent, or Firm* — Patrick Laycock; Rodman and Rodman LLP (57) ABSTRACT

Ophthalmic devices are used to treat a variety of eye conditions. Such devices include intraocular lens (IOL) implants, contact lenses, intraocular telescopes, and the like. Such ophthalmic devices typically include one or more lenses to interact with visible light. According to an aspect of the disclosure, there is provided an ophthalmic device comprising a biocompatible polymer body and a metalens. The metalens is encapsulated by the polymer body. The metalens comprises a substantially transparent substrate and a plurality of subwavelength structures arranged on the substrate in a pattern to interact with visible light. subwavelength structures comprise a dielectric material such as titanium dioxide.

19 Claims, 6 Drawing Sheets

(56) References Cited

U.S. PATENT DOCUMENTS

2018/0284428 A1 10/2018 Guenter
2019/0154877 A1 5/2019 Capasso et al.

OTHER PUBLICATIONS

International Search Report and Written Opinion that issued on PCT/CA2017/051570.
M. Khorasaninejad, et al., in "Visible Wavelength Planar Metalenses Based on Titanium Dioxide", IEEE Journal of Selected Topics in Quantum Electronics, vol. 23, No. 3, May/Jun. 2017.
F. Aieta, et al., "Multiwavelength achromatic metasurfaces by dispersive phase compensation", Science, vol. 347, pp. 1342-1345, 2015.
Joseph A. Lemire et al., "Antimicrobial activity of metals: mechanisms, molecular targets and applications" Nature Reviews Microbiology, vol. II, No. 6, pp. 371-384; Jun. 13, 2013.
M. Khorasaninejad et al., "Super-Dispersive Off-Axis Meta-Lenses for Compact High Resolution Spectroscopy" Nano Lett. 2016, 16, 3732-3737.
Wei Ting Chen et al., "A broadband achromatic metalens for focusing and imaging in the visible", Nature Nanotechnology, vol. 13, pp. 220-226 (2018).
Andrea Di Falco et al., "Flexible metamaterials at visible wavelengths", 2010 New J. Phys. 12 113006.
Wang et al., "Wide-band achromatic metalens for visible light by dispersion compensation method" 2017 J. Phys. D: Appl. Phys. 50 455101.
H. Chen et al., "A review of metasurfaces: physics and applications", pp. 1-44, May 26, 2016.
C. Borkhataria, "Will your next spectacles have Metal lenses? Harvard researchers reveal radical new material that could replace glass in everything from phones to eyewear", Daily Mail, Feb. 8, 2017.
L. Burrows, "Metalens works in the visible spectrum, sees smaller than a wavelength of light", News and Events, Harvard, John A. Paulson School of Engineering and Applied Sciences, Jun. 2, 2016.

\* cited by examiner

OPHTHALMIC DEVICES AND METHODS

FIELD OF THE DISCLOSURE

The present disclosure relates to ophthalmic devices including intraocular lens implants, contact lenses and the like. More particularly, the present disclosure relates to ophthalmic devices including one or more metalenses.

BACKGROUND

Ophthalmic devices are used to treat a variety of eye conditions. Such devices include intraocular lens (IOL) implants, contact lenses, corneal inlays, intraocular telescopes, and the like. Such ophthalmic devices typically include one or more lenses to interact with visible light. For example, a contact lens is placed on the eye to correct an eyesight condition (e.g. near or far-sightedness). An IOL implant is implanted within the eye. An IOL implant may replace the natural lens in the eye, or the natural lens may remain. For example, a phakic IOL implant is implanted in the eye without altering the natural lens of the eye. Ophthalmic devices typically utilize refractive or diffractive lenses.

Implanting IOLs is an invasive procedure that requires creating an incision in the eye. Reducing the thickness of IOLs may reduce complications associated therewith. The minimum thickness of a conventional ophthalmic device may be limited by the refractive lens.

SUMMARY

According to an aspect of the disclosure, there is provided an ophthalmic device comprising: a biocompatible polymer body; and a metalens encapsulated within the polymer body, the metalens comprising: a substantially transparent substrate; and a plurality of subwavelength structures arranged on the substrate in a pattern to interact with visible light, the subwavelength structures comprising a dielectric material.

In some embodiments, the device comprises an implant or inlay for an eye.

In some embodiments, the implant or inlay comprises one of: an intraocular lens implant; and an intracorneal lens inlay.

In some embodiments, the device comprises the intraocular implant, and the intraocular implant comprises one of: a phakic intraocular lens implant; and a posterior chamber intraocular lens implant.

In some embodiments, the device comprises a contact lens.

In some embodiments, the dielectric material is titanium dioxide.

In some embodiments, the polymer body is hydrophobic.

In some embodiments, the polymer body comprises one of: acrylic polymer and silicone hydrogel.

In some embodiments, the plurality of subwavelength structures comprises nanopillars.

In some embodiments, the substrate comprises a polymer substrate.

In some embodiments, the polymer substrate is flexible.

In some embodiments, the polymer substrate comprises at least one of: silicone, acrylic and a hydrogel.

In some embodiments, the metalens is configured to correct an eyesight condition.

In some embodiments, the subwavelength structures each have at least one respective dimension that is less than a wavelength of the visible light.

In some embodiments, the at least one dimension comprises at least one of height, width and thickness of the subwavelength structure.

In some embodiments, the metalens interacts with the visible light over a range of visible light wavelengths.

According to another aspect of the disclosure, there is provided a method for making an ophthalmic device comprising: providing a metalens comprising a substantially transparent substrate and a plurality of subwavelength structures arranged on the substrate in a pattern to interact with visible light, the subwavelength structures comprising a dielectric material; and encapsulating the metalens in a biocompatible polymer body.

In some embodiments, providing the metalens comprises fabricating the metalens using an electron beam lithography (EBL) process.

Other aspects and features of the present disclosure will become apparent to those ordinarily skilled in the art upon review of the following description of the specific embodiments.

BRIEF DESCRIPTION OF THE DRAWINGS

Aspects and embodiments of the disclosure will now be described in greater detail with reference to the accompanying diagrams, in which.

DETAILED DESCRIPTION

A conventional ophthalmic device, such as an intraocular lens (IOL) implant, intracorneal implant or inlay, or a contact lens, may include a refractive lens to interact with visible light. The minimum thickness of the device may be limited by the geometric requirements of the one or more refractive lenses. It may be desirable to reduce the thickness of such devices.

Conventional surgical incisions made by blades or lasers for insertion of an IOL device may have a minimum size that is limited by the IOL's size, thickness and foldability. Reducing the thickness of the device may consequently reduce the necessary size of the incision in the eye. Reducing the size of the incision and the device may, in turn, reduce trauma to the eye such as scarring and induced astigmatism resulting from surgery. Foldable lenses or IOL implants comprising polymers (e.g. hydrophobic acrylic, silicone, hydrogels etc.) may further reduce the required incision size.

Various other benefits may arise from reducing the size of ophthalmic devices. For example, a thinner corneal inlay may require a smaller "pocket" to hold it, which may be less disruptive to the normal cornea. As another example, reducing the thickness of contact lenses or corneal inlays may result in greater oxygen permeability (dK, dKt) and a healthier cornea. As yet another example, conventional intraocular telescopic housings are relatively large and may require large incisions with sutures to close. A smaller IOL telescope may allow smaller, possibly sutureless incisions, which may result in fewer surgical complications. As still another example, in the case of a phakic IOL implant, there is less room since the natural lens is still in place. Reducing the thickness of a phakic IOL implant may provide advantages, regardless of whether the implant is in the anterior chamber, fixed to the iris, or in the posterior chamber sulcus.

Figure 3:
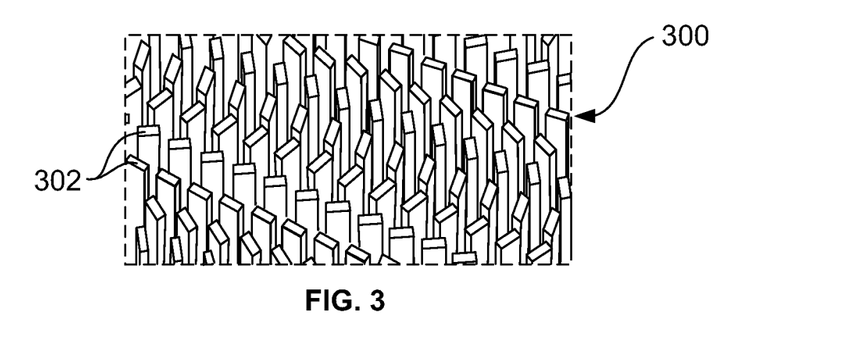
FIG. 3 is an enlarged perspective partial view of an example array of nanofins of a metalens.

A "metalens" is a lens including an array of structures on a substrate that interact with electromagnetic radiation. Specifically, the structures have dimensions that are less than the wavelength(s) of the radiation and are arranged in a pattern which alters an incoming wavefront in a non-refractive, non-diffractive manner by virtue of the composition, shape, orientation, height and diameter of the structures. Structures having such dimensions are referred to herein as "subwavelength structures". To interact with electromagnetic radiation in the visible spectrum (i.e. visible light), the subwavelength structures have dimensions such as height, width and/or spacing in the nanometer range. Thus, such structures may be referred to as nanostructures. Nanostructures may be in the form of nanofins or other nanopillars which act as sub-wavelength light phase shifters rather than traditional lenses. The term "nanopillar" refers to any structure with one or more subwavelength dimensions (height, width, thickness) that extends away from the substrate. The term "nanofin" refers to a nanopillar with a generally fin-like shape. For example, nanofins may have a generally rectangular prism-like shape as shown in FIG. 3. A metalens may also be referred to as a "planar lens".

The dimensions of the subwavelength structures may allow a metalens to be much thinner than a refractive lens. A metalens may, thus, be referred to as "nano-thin" or "ultrathin". Metalenses have been proposed for use in various electronic devices such as cellphone/camera lenses, virtual reality headsets, LED focusing devices, laser lenses, holograms, diffraction gratings, microscope lenses, spectrometers etc.

However, many conventional metalenses are not suitable for use in ophthalmic devices, which require biocompatibility and may require functioning over a broad range of visible wavelengths. The term "biocompatible" herein means generally not harmful to living human tissue. Some metalenses have been designed to function in the visible spectrum only at a particular wavelength or in a very narrow wavelength range. Some existing metalenses that do interact with visible light include metal nanostructures. Such metalenses are subject to magnetic attraction and thus unsuited to use in or on the eye.

According to an aspect of the present disclosure, there is provided an ophthalmic device comprising a metalens encapsulated in a biocompatible polymer body, such as hydrophobic acrylic body. The metalens comprises a plurality of subwavelength dielectric structures arranged on a substrate to interact with visible light. The substrate may, for example, be a substantially transparent polymer or another light-transmissive material. The dielectric may be titanium dioxide (TiO2). The subwavelength dielectric structures may be nanofins or nanopillars arranged to function over a range of wavelengths. The resulting metalens-based ophthalmic device may be thinner than conventional devices. As discussed above, reducing the thickness of such devices may be advantageous (smaller incision size required, etc.).

Example metalens structures including TiO2 nanostructures to interact with visible light over a suitable spectrum range are described by Mohammadreza Khorasaninejad, et al., in "Visible Wavelength Planar Metalenses Based on Titanium Dioxide, IEEE Journal of Selected Topics in Quantum Electronics, Vol. 23, No. 3, May/June 2017, which is incorporated by reference herein in its entirety. Example TiO2-based metalenses are also described by Byrnes et al. in U.S. Patent Application Publication No. 2017/082263, which is incorporated by reference herein in its entirety.

The metalenses described herein may be configured to interact with visible light having wavelength in the range of 380 to 660 nm. Mohammadreza Khorasaninejad, et al. show results for TiO2 metalenses at wavelengths of 660 nm, 532 nm and 405 nm and state that the operating bandwidth of such metalenses may be expanded by dispersion engineering to a multi-wavelength regime and potentially for a continuous wavelength range. See also F. Aieta, M. A. Kats, P. Genevet, and F. Capasso, "Multiwavelength Achromatic Metasurfaces by Dispersive Phase Compensation", Science, vol. 347, pp 1342-1345, 2015, which is incorporated herein by reference in its entirety.

The combination of TiO2 metalens nanostructures and a hydrophobic acrylic body may provide particular advantages for IOL implants and other ophthalmic devices. For example, TiO2 (and other dielectrics) is non-magnetic and, thus, more suitable for use in an intraocular implant than metal. TiO2 also has been shown to be suitable for metalenses that function over a suitably broad range of the visible light spectrum. TiO2 is also biocompatible and bioinert and has been used in other types of biomedical devices such as dental implants, orthopedic implants, catheters, etc. TiO2 may have negligible optical absorption in the visible spectrum. Other potential benefits of TiO2 include its high index of refraction (close to diamond), high melting point, and antimicrobial properties. See for example, Joseph A. Lemire et al. "Anti microbial Activity of Metals: Mechanisms, Molecular Targets and Applications" Nature Reviews Microbiology, Vol. II, No. 6, pages 371-384; Jun. 13, 2013, the entirety of which is incorporated by reference. TiO2, when deposited, may be strongly adherent to the substrate and chemically impermeable.

Furthermore, hydrophobic acrylic may be a beneficial material for the body that encapsulates the metalens because it is biocompatible and has been shown as safe in conventional ophthalmic devices. Thus, a hydrophobic acrylic encapsulating body may be safe and facilitate obtaining regulatory approval.

The subwavelength structures of the metalens are not limited to TiO2. In other embodiments, the subwavelength structures may be made of one or more other dielectric materials including, but not limited to, quartz, Gallium Nitride (GaN), and silicon nitride.

The substrate of the metalens may be any suitable substantially light-transmissive or transparent material. Some specific examples of substrate material include, but are not limited to, substantially transparent polymer such as silicone, hydrophobic or hydrophilic acrylic, or a hydrogel. The substrate may also be a High Refractive Index Polymer (HRIP) nano-composite material, which may be an organic matrix with high refractive inorganic nanoparticles combined to create a substrate. In some embodiments, the substrate may have a chromophore or coating to filter ultraviolet (UV) light to protect the eye from UV exposure.

The substrate may be substantially rigid in some embodiments. In other embodiments, the substrate may be a flexible, bendable material (e.g. silicone, hydrophobic or hydrophilic acrylic, or a hydrogel). A bendable or foldable substrate may provide additional versatility. For example, metalens-based IOL implants that are thin and sufficiently foldable may be rolled and injected into the eye through a cartridge, further reducing incision size.

The term "substantially transparent" as used herein does not require absolute transparency. Rather, for example, a tinted and/or other highly transmissive material may be considered substantially transparent in that it is suitable for use in ophthalmic devices.

The polymer body that encapsulates the metalens is not limited to hydrophobic acrylic, and other suitable biocompatible polymer materials may be used. For example, other possible body materials include Silicone Hydrogel (SiHy), polymethylmethacrylate (PMMA), hydrophobic acrylic, hydrophilic acrylic, silicone and collamer.

Figure 1:
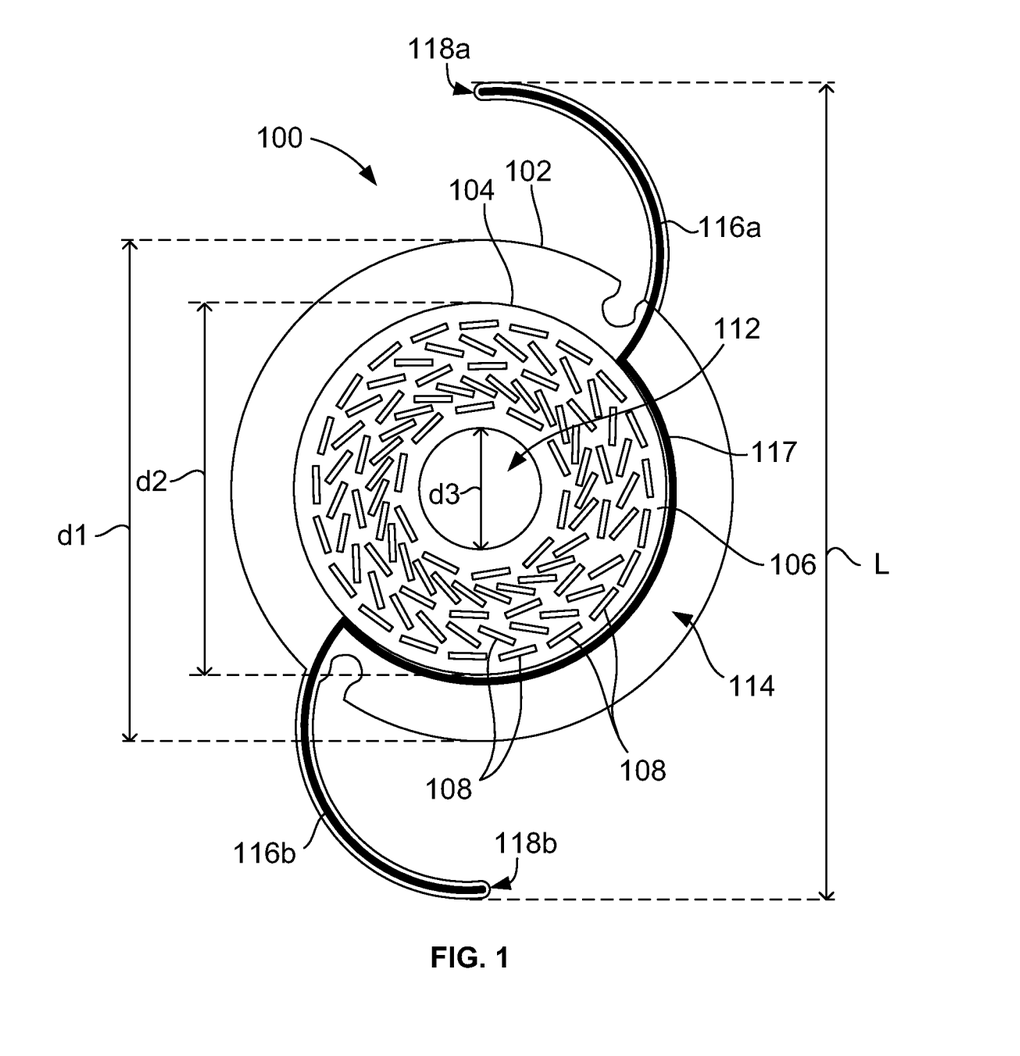
FIG. 1 is a front view of an example IOL implant according to some embodiments.

FIG. 1 is a front view of an example IOL implant 100 according to some embodiments. The implant 100 includes a hydrophobic acrylic polymer body 102 and a metalens 104 encapsulated by the body 102. The metalens 104 comprises a polymer substrate 106 with an array of TiO2 subwavelength structures 108 arranged thereon. The subwavelength structures 108 are arranged on the substrate in a pattern to interact with visible light.

The metalens 104 in this example is planar disc-shaped having a diameter (d2) of approximately 6 mm (although the diameter may vary in other embodiments). The subwavelength structures 108 are arranged in a pattern that extends radially about a center axis 124 (shown in FIG. 2) of the metalens 104 for an iris-like distribution. The metalens in this example defines a circular center area 112 that does not include the subwavelength structures. The subwavelength structures 108 are not included in the center area 112 in this embodiment because axial and paraxial rays passing therethrough may not require refraction to focus. The center area 112 has a diameter (d3) of approximately 2 mm, although embodiments are not limited to this dimension. In other embodiments, the center area 112 may be larger or smaller. Thus, in some embodiments, the metalens 104 may include subwavelength structures in the region occupied by the center area 112 in FIG. 1.

The body 102 is generally disc-shaped and extends radially beyond the metalens 104 to form an outer annulus portion 114. The body 102 may stabilize the subwavelength structures 108 suspended therein, and may also help maintain alignment of the metalens 104.

In some embodiments, the metalens 104 may be foldable or bendable. The implant 100 may be collapsed or folded (e.g. for insertion) and contained within a cartridge before implantation in the eye. During the implantation procedure, the implant 100 may be ejected from the cartridge into the eye, after which the implant 100 may unfold within the eye at a desired position for use, for example. The cartridge may have a size that corresponds to the incision made in the eye. The body 102 of the implant 100 may have a form "memory" position to which it returns when unfolding.

The subwavelength structures 108 in this example are nanofins. As will be apparent to a person skilled in the art, the size of the structures 108 are not shown to scale, but are substantially enlarged in FIG. 1 for illustrative purposes. A person skilled in the art will also appreciate that in the metalens 104 will typically include many times more subwavelength structures 108 than are shown in FIG. 1 (possibly on the order of one million structures 108 per square millimeter or more).

By way of example, the diameter (d1) of the body 102 may be approximately 8 mm (although embodiments are not so limited), while each structure 108 may have height, width and/or thickness in the range of 10 s to 100 s of nanometers. A nanofin-type subwavelength structure may be generally rectangular prism-shaped. For example, a nanofin sized to have a peak response at the wavelength of green light (532 nm) may be 600 nm high by 250 nm wide by 95 nm thick (although embodiments are not limited to these particular dimensions). The nanofins may, for example, be spaced approximately 600 nm apart. The nanofins (or other subwavelength structures) may be arranged radially about the center axis 124 at various tilt angles relative to the radial direction. The separation between the structures 108 may similarly be in the range of nanometers.

The thickness of the metalens 104 may be on the order of microns, depending on the thickness of the substrate 106. Even including the body 102 that encapsulates the metalens 104, the overall thickness of the IOL implant 100 may be substantially less than conventional IOL implants, which typically have a thickness of approximately one millimeter or more.

The metalens may include multiple zones, with each zone having a respective distribution of subwavelength structures. The subwavelength structures in one zone may have one or more dimensions and/or distribution patterns that differ from one or more other zones. Embodiments are not limited to a particular pattern, dimension, or distribution of the subwavelength structures.

The subwavelength structures 108 in the IOL implant 100 of FIG. 1 are TiO2, although embodiments are not limited to TiO2 structures. TiO2 may be particularly suited for use in ophthalmic devices such as the IOL implant 100 of FIG. 1. TiO2 subwavelength structures 108 may be substantially lossless for light in the visible spectrum. TiO2 also has a high index of refraction (approximately 2.37 for 550 nm wavelength light), and metalenses using this dielectric may have high conversion efficiency. The term "conversion efficiency" herein refers to the amount of visible light entering the system when compared to the amount in the final focal point. Losses may occur from reflection, scattering, absorption, diffraction, etc. Mohammadreza Khorasaninejad, et al. referenced above disclose up to 86% actualized and 95% simulated conversion efficiency for TiO2 metalenses. Such metalenses may also have a high numerical aperture (NA) (e.g. NA=0.8) and may be capable of focusing light into diffraction limited spots 1.5× smaller than commercial 100× objective lenses, such as the Nikon™ CFI 60. Furthermore, TiO2 may be deposited on certain materials, atomic layer by layer by existing chip manufacturing technology.

The IOL implant 100 also includes optional haptics 116a and 116b, which may facilitate handling, centration and capsular bag stabilization of the IOL implant 100. The haptics 116a and 116b are formed by a haptic spine 117. The haptic spine 117 may be poly(methyl methacrylate) (PMMA), for example. PMMA is more rigid than hydrophobic acrylic, but still somewhat flexible. PMMA also has a "form memory" such that it may help stabilize the shape of the implant 100 while still allowing the implant 100 to be folded. PMMA also has the advantage of being FDA approved. In some embodiments, the haptics 116a and 116b may be formed by multiple sections of PMMA rather than the continuous spine 117. In an alternative embodiment, the implant may comprise a capsular tension ring (CTR) delivery system. A CTR system includes a foldable, injectable ring instead of PMMA haptics of the type shown in FIGS. 1 and 2.

The body 102 in this example also encapsulates the haptics 116a and 116b. In other embodiments, the haptics 116a and/or 116b may not be covered/encapsulated by the polymer body 102.

The overall length (L) of the IOL implant 100 (between ends 118a and 118b of the haptics 116a and 116b) in this example is approximately 13 mm. However, embodiments are not limited to a particular size or shape.

The IOL implant 100 may optionally be formed with a posterior convexity, which may enhance three-point fixation. For example, the substrate 106 of the metalens 104 may have a convex posterior face.

Figure 2:
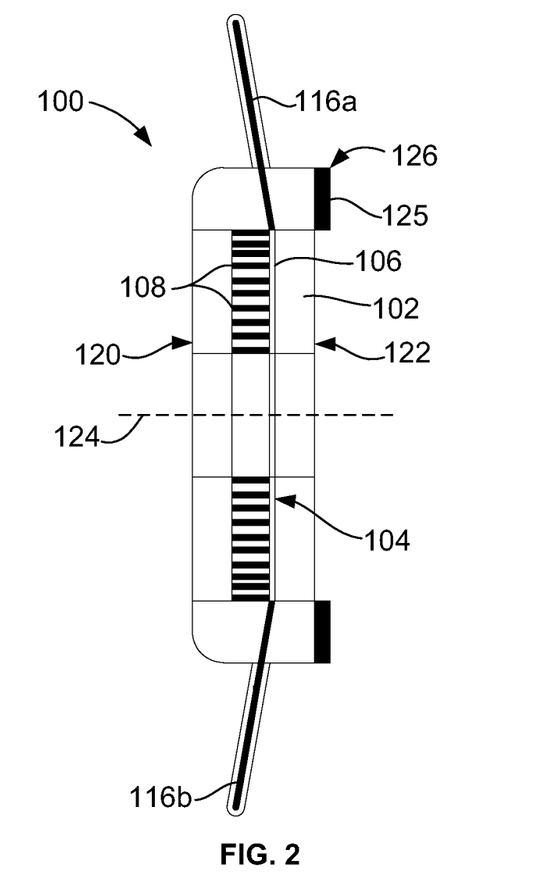
FIG. 2 is a side view of the IOL implant of FIG. 1.

FIG. 2 is a side view of the IOL implant 100 of FIG. 1. The IOL implant 100 has an anterior face 120 and a posterior face 122. Again, the subwavelength structures 108 of the metalens 104 are not shown to scale for illustrative purposes. The substrate 106 in this example is flat, but may have posterior convexity in other embodiments. The hydrophobic acrylic body 102 encapsulates and stabilizes the metalens 104 and also covers the haptics 116a and 116b. As shown in FIG. 2, the example haptics 116a and 116b in this embodiment are angled forward (about 10 degrees in this example). The haptics 116a and 116b may provide three-point fixation.

The center axis 124 is shown in FIG. 2. The metalens 104 extends radially about the center axis.

FIG. 3 is an enlarged perspective partial view of an example array 300 of nanofins 302 of a metalens. The array 300 is only partially shown and extends beyond the stippled line border of FIG. 3. Similar nanofin arrays are shown by M. Khorasaninejad et al. "Super-Dispersive Off-Axis Meta-Lenses for Compact High Resolution Spectroscopy" Nano Lett. 2016, 16, 3732-3737, the entire content of which is incorporated by reference. The nanofins 302 are generally rectangular-prism-shaped extensions from a substrate (not visible). The subwavelength structures 108 of the IOL implant 100 shown in FIGS. 1 and 2 may be in a form similar to the nanofins 302 shown in FIG. 3. For example, the array 300 may be representative of a small portion of the metalens 104 in FIGS. 1 and 2. However, embodiments are not limited to the particular arrangement of nanofins shown in FIG. 3. The specific arrangement/pattern of the subwavelength structures may vary and is dependent upon the desired refractive outcome. Embodiments are not limited to any particular configuration of the subwavelength structures.

To determine a desired layout of the subwavelength structures 108, an eye may be measured pre-operatively (e.g. by ultrasound or laser biometry). The measurement may determine, for example, the corneal curvature, the anterior chamber depth, the axial length to the retina, and/or, depending on the type of IOL implant, the positioned refractive index of the IOL implant to be inserted. A dioptric strength of the IOL may be calculated based on the eye measurement. For example, for a given eye, a lens from a first manufacture may require a dioptic strength of 21.5D to achieve emmetropia. For a second lens manufacturer, a dioptic strength of 22.5D may be required for the same eye.

Computer software may then be used to determine the dimensions and arrangement of the subwavelength structures based on the requirements obtained as a function of the eye measurement process. One example of suitable software is Lumerical™ simulation software. The software may, for example, define the subwavelength pattern/arrangement to achieve the equivalent focal point to the refractive equivalent dioptric strength (21.5D or 22.5D in this example). This may be equivalent of traditional convex, concave, astigmatic (toric) or multifocal configurations. However, the variable in lens configuration is not curvature (as for refractive lenses) but rather the height, width, tilt and separation of the subwavelength structures to achieve the same focus. A metalens with the particular configuration determined by the Lumerical™ computer simulation software may then be fabricated. Again, it is to be understood that embodiments are not limited to any particular arrangement or pattern of subwavelength structures, or to any method of determining the particular arrangement or pattern.

Turning again to FIGS. 1 and 2, encapsulation of the metalens 104 and haptics 116a and 116b in the hydrophobic acrylic body 102 may provide biocompatibility and ocular immune sequestration. Since hydrophobic acrylic is conventionally used in ophthalmic devices, such as contact lenses and intraocular lens implants, the use of hydrophobic acrylic may, thus, facilitate regulatory approval of metalens-based ophthalmic devices described herein. As also mentioned above, TiO2 subwavelength structures may have antimicrobial properties, and other medical and dental devices use TiO2 for its non-toxicity, biocompatibility and biostability.

Optionally, the implant 100 includes a 360 degree posterior optic epithelial lens barrier 125 (visible in FIG. 2). The barrier 125 has a 90 degree outer edge 126 in this embodiment and may inhibit lens epithelial migration and may reduce posterior capsular opacification.

The implant 100 may also include various other features not shown including, but not limited to, ultraviolet (UV) protection, blue filters, antireflection coatings, etc. In the case of a phakic IOL implant, the implant may include vaulting. Other embodiments may also include multifocal platforms. In some embodiments, the ophthalmic device may be a telescopic IOL implants.

In some embodiments, the metalens-based ophthalmic devices described herein may not have designated front and back surfaces and may be reversible.

Figure 4:
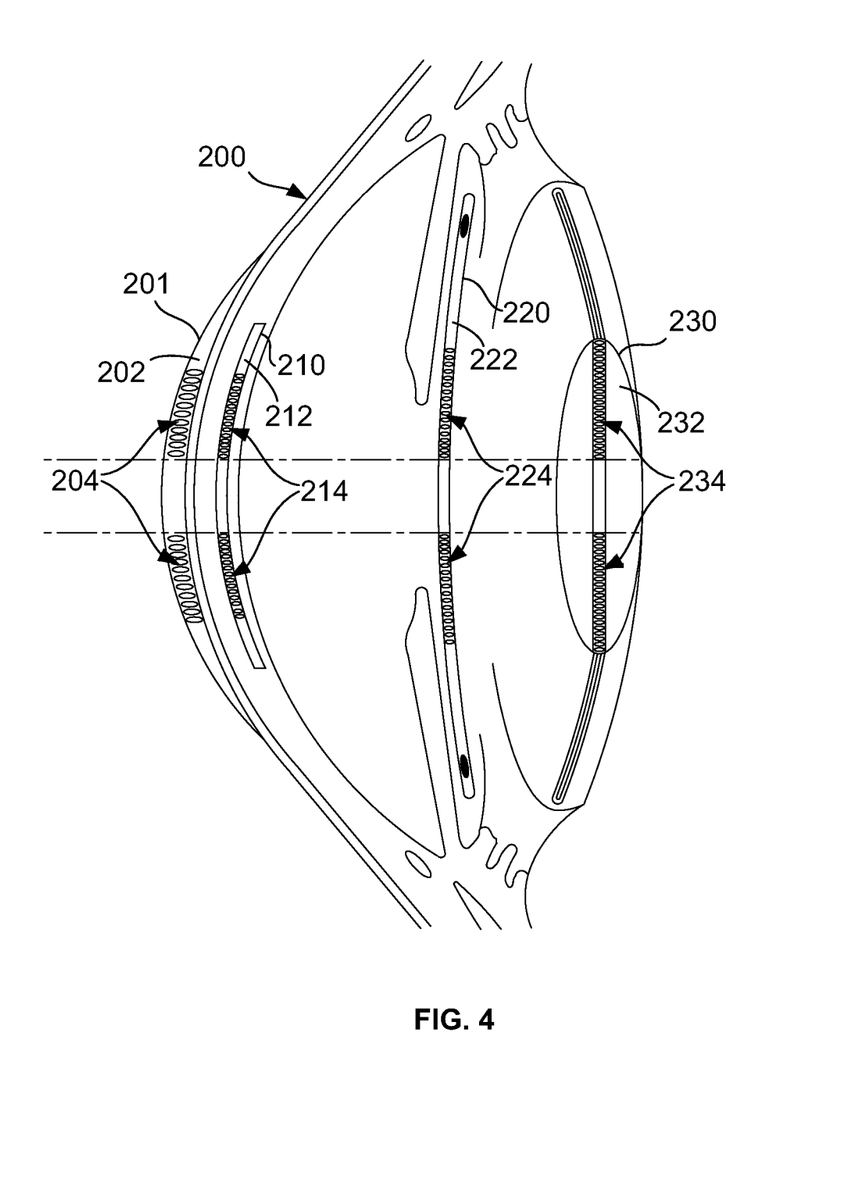
FIG. 4 is a side cross-sectional view of a human eye showing example embodiments of ophthalmic devices.

FIG. 4 is a cross-sectional view of a human eye 200 showing a few example embodiments of ophthalmic devices 201, 210, 220 and 230 are shown.

In one embodiment, the ophthalmic device 201 is a contact lens including a polymer body 202 and a metalens (not visible) encapsulated therein within metalens zone 204. The metalens zone 204 is visually represented by an array of ellipses in FIG. 4, although it is to be understood that the metalens within zone 204 is typically significantly thinner than the zone 204 as shown. The ellipses indicating the zone 204 are simply used to show the general region in which the metalens may be contained within the corresponding body 202. The remaining ophthalmic devices 210, 220 and 230 in FIG. 4 are similarly illustrated.

The body 202 is Silicone Hydrogel (SiHy) in this embodiment, but the body 202 may comprise other suitable materials (e.g. acrylic) in other embodiments. SiHy materials such as the Hydra Acuvue™ series with high Oxygen Permeability (Dk) and Oxygen Transmissibility (Dk/t) may permit easy oxygen permeability/transmissibility with a higher modulus and rigidity. A metalens-based device may be ultrathin and, being planar, may enhance the Dk and/or Dk/t.

SiHy material on a metalens platform might also be used as an intracorneal inlay after a femto stromal plane is created. Ultrathin inlays with or without fenestrations may be more oxygen and nutrient transmissible and may be additive rather than subtractive. A pocket in the cornea is created with a laser to receive a metalens inlay that is inserted surgically.

The metalens inlay is an "additive" procedure to correct a pre-existing refractive error. On the other hand, laser refractive surgery is a "subtractive" procedure that removes corneal tissue by laser-sculpting. An example of laser refractive surgery is Small Incision Lenticule Extraction (SMILE), which is a subtractive procedure where a lenticule is cut with a laser and removed. By contrast, an inlay only requires space enough to sit. Another example of subtractive laser refractive surgery is Laser-Assisted in Situ Keratomileusis (LASIK). One benefit of additive procedures, such as inserting an inlay, is reversibility. For example, the inlay may be removed. On the other hand, subtractive procedures such as laser refractive surgery are permanent.

In another embodiment shown in FIG. 4, the ophthalmic device 210 is a Femto Pocket Intracorneal inlay comprising a body 212 encapsulating a metalens (not shown) within metalens zone 214. The body 212 in this example may be Silicone Hydrogel (SiHy), acrylic or another suitably biocompatible material. Intracorneal inlays may also be referred to as intracorneal implants.

In another embodiment, the ophthalmic device 220 is a Phakic Sulcus IOL implant comprising a body 222 encapsulating a metalens (not shown) within metalens zone 224. The body 222 may, for example, by hydrophobic acrylic or another suitably biocompatible material. Phakic IOL's may be used for high refractive errors not correctable by LASIK or SMILE Conventional phakic IOL implants may have risks of infection (endophthalmitis), glaucoma (pupillary block by the implant) and cataract (from implant-lens contact in the eye). A metalens-based phakic IOL implant, as disclosed herein, may be thinner and lighter than conventional implants, which in turn may reduce the likelihood and/or severity of such complications.

In another embodiment, the ophthalmic device 230 is a Posterior Chamber (PC) IOL implant comprising a body 232 encapsulating a metalens (not shown) within metalens zone 234. The body 232 may, for example, be hydrophobic acrylic. PC IOL's by STAAR and IOL Tech/Carl Zeiss Meditech may vault and cause angle closure/pupil block/PDS if too long. If too short, they may decenter or cause cataracts. On the other hand, a metalens-based PC IOL (such as device 230) with hydrophobic acrylic encapsulation could utilize PMMA as a hapic or a CTR adapted for the sulcus with a central vault to protect the lens.

The metalenses of the devices 201, 210, 220 and 230 may each be similar to the metalens 104 shown in FIGS. 1 and 2, including a substrate with a plurality of subwavelength structures thereon to interact with visible light.

Figure 5:
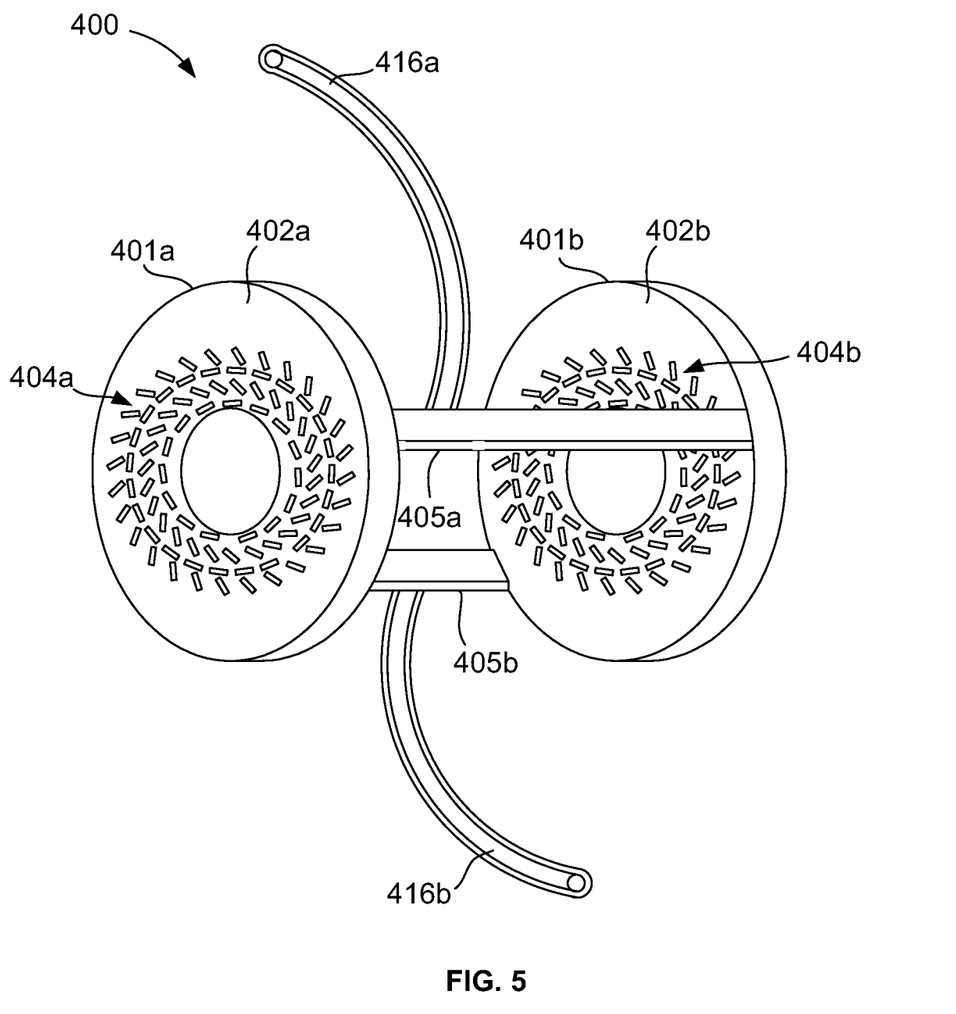
FIG. 5 is a side perspective view of an ophthalmic device according to another embodiment.
Figure 6:
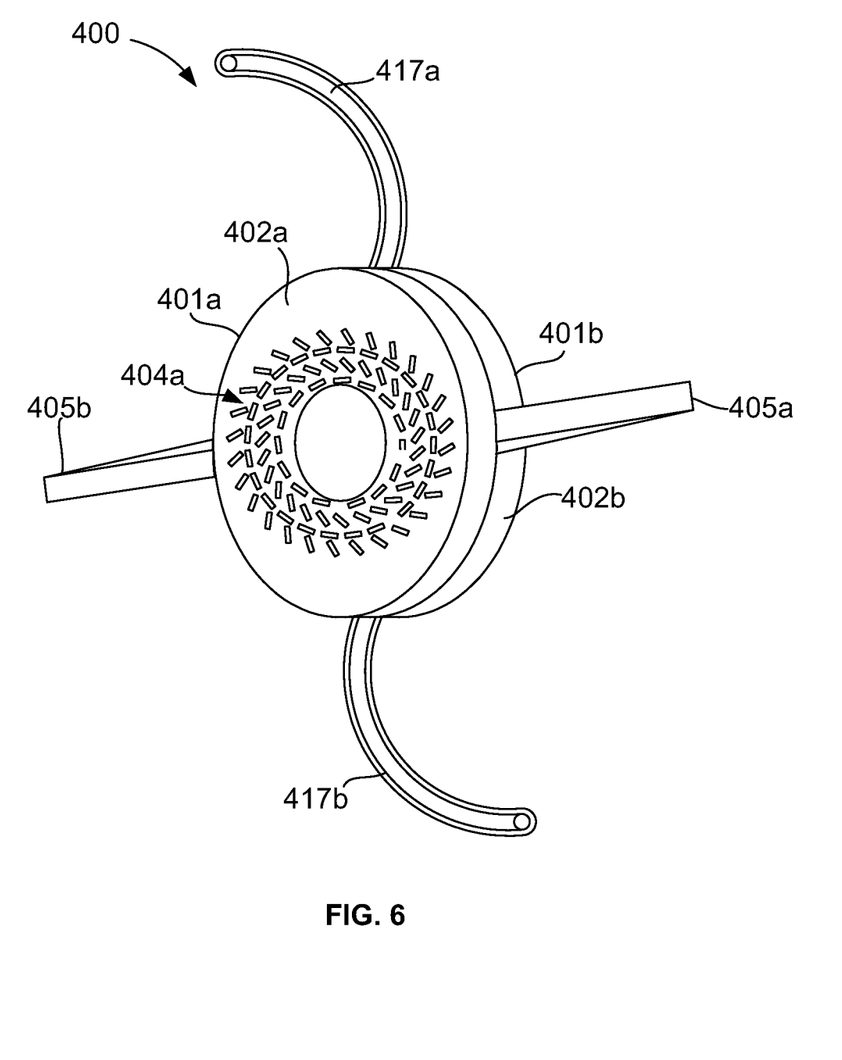
FIG. 6 is another side perspective view of the ophthalmic device of FIG. 5.

FIGS. 5 and 6 are side-perspective views of an intraocular telescope 400 according to an embodiment. The intraocular telescope 400 may be used to treat macular degeneration, for example. The intraocular telescope 400 may be smaller than a conventional intraocular telescope.

The intraocular telescope 400 includes first and second portions 401a and 401b. The first portion 401a may be referred to as the "eyepiece lens" portion and the second portion 401b may be referred to as the "objective lens" portion. Each portion 401a and 401b includes a respective metalens 404a and 404b encapsulated in a respective polymer body 402a and 402b. The first and second portions 401a and 401b are interconnected by first and second snap-in bridge pillars 405a and 405b. The snap-in bridge pillars 405a and 405b fold to provide the folded position shown in FIG. 6 and straighten to provide the extended position shown in FIG. 5. The intraocular telescope may, thus, be folded to a fixed focal distance between the eyepiece and objective lens.

Conventional IOL telescopes typically comprise a one-piece, large implantable device. This requires a large incision to implant when compared to other types of IOL implants. The IOL telescope 400 in FIGS. 5 and 6 on the other hand collapses or "spoons" the first and second portions 401a and 401b (in the folded position of FIG. 6) for insertion. Thus, the incision required to insert the IOL telescope 400 may be smaller (possibly even sutureless) compared to conventional IOL telescopes. The snap-in bridge pillars 405a and 405b are sized to establish the desired separation between lenses when in their extended positions (shown in FIG. 5). The snap-in bridge pillars 405a and 405b may provide a fixed, non-adjustable focus. However, in other embodiments, an adjustment mechanism to allow adjustment of the separation may be used to provide multiple separation distances and/or autofocus functionality.

In FIG. 5, the intraocular telescope 400 is shown with optional PMMA haptics 416a and 416b. The haptics 416a and 416b are similar to the haptics 116a and 116b in FIG. 1. The haptics 416a and 416b may stabilize the IOL telescope 400 (e.g. within the capsular bag of the eye). The haptics 416a and 416b are attached to the bridge pillars 405a and 405b respectively. Embodiments are not limited to any particular configuration of the haptics 416a and 416b.

In FIG. 6, the intraocular telescope 400 is shown with optional haptics 417a and 417b in an alternate configuration. The haptics 417a and 417b are similar to the haptics 416a and 416b in FIG. 5, but attached to the second portion 401b of the intraocular telescope 400 rather than the bridge pillars 405a and 405b. Alternatively, one or more haptics may be attached to the first portion 401a of the intraocular telescope 400.

In still other embodiments, the ophthalmic device may be a keratoprosthesis. A keratoprosthesis incorporating a metalens may have reduced weight, thickness and complexity compared to conventional designs.

Figure 7:
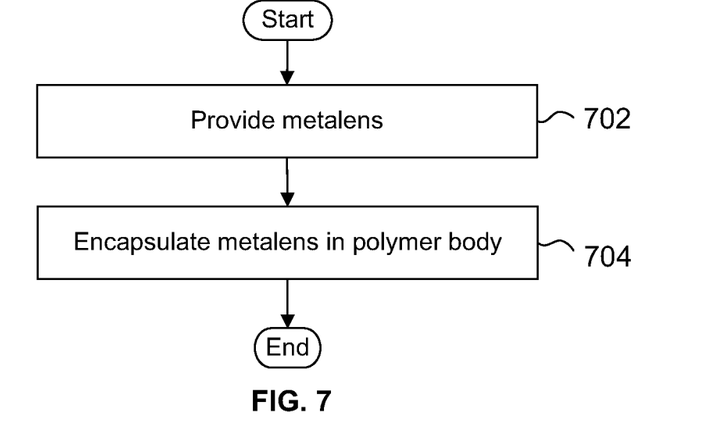
FIG. 7 is a flowchart of a method for making an ophthalmic device according to some embodiments.

FIG. 7 is a flowchart of a method for making an ophthalmic device according to some embodiments.

At block 702, a metalens is provided. Providing the metalens may comprise manufacturing, purchasing or otherwise obtaining the metalens. The metalens includes a plurality of dielectric subwavelength structures arranged on a substrate to interact with visible light. The metalens may be similar to the metalens 104 of FIGS. 1 and 2, for example. An example method for making the metalens is described below with reference to FIG. 8.

At block 704, the metalens is encapsulated in a polymer body. The polymer body may comprise hydrophobic acrylic, Silicone Hydrogel (SiHy) or any other suitable biocompatible material, as described above. The device may be in the form of a contact lens, IOL implant, or other ophthalmic device (such as the devices 100, 201, 210, 220, 230 or 400 of FIGS. 1, 2 and 4 to 6). The encapsulation may include a molding process.

In some embodiments, technology similar to existing silicon chip manufacturing processes may be used or adapted for creating a metalens for an ophthalmic device. An example EBL process for fabricating a metalens is described by Mohammadreza Khorasaninejad, et al. (2017), which is incorporated herein by reference.

Figure 8:
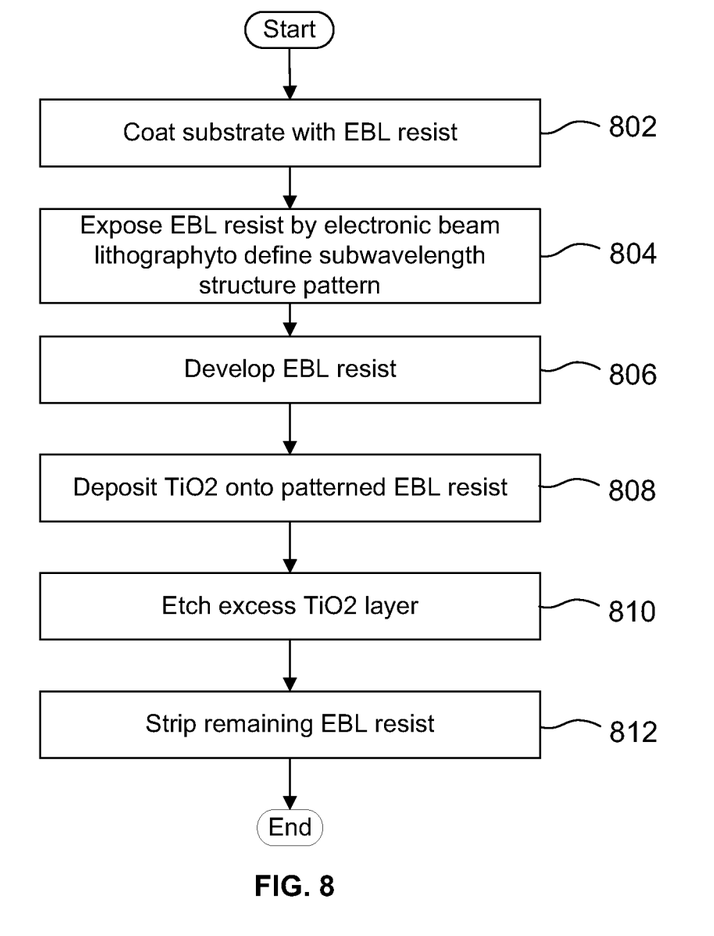
FIG. 8 is a flowchart of a method for making a metalens for an ophthalmic device using an electron beam lithography (EBL) process according to some embodiments.

FIG. 8 is a flowchart of a method for making a metalens for an ophthalmic device using an electron beam lithography (EBL) process according to some embodiments. Embodiments are not limited to the particular EBL process described below. The metalens may also be fabricated using a non-EBL process (e.g. UV lithography) in other embodiments.

At block 802, a polymer substrate is coated with a layer of resist. The resist may, for example, be spin-coated on the substrate. The resist in this example is an EBL resist such as ZEP 520A resist. The thickness of the resist layer may determine the height of the nanostructures to be formed.

At block 804, the resist is exposed by EBL, defining the pattern of the nanostructures in the resist. Alternatively, deep ultraviolet (UV) lithography may be used to pattern the resist. The pattern for the lithography step may generated using commercially available software (e.g. from Lumerical Inc.™).

At block 806, the resist is developed in o-xylene (e.g. 99% o-xylene). This step removes resist according to the lithographed pattern and leave holes or gaps that correspond to the geometry of the intended nanostructures. The remaining resist on the substrate at this stage may be referred to as "patterned" resist.

At block 808, TiO2 is deposited onto the patterned resist. The deposition may be performed by atomic layer deposition (ALD). The TiO2 atomic layer deposition fills the gaps within the patterned resist to form subwavelength structures of the desired shape, diameter, height, tilt and spacing. These subwavelength structures or short wavelength structures (SWS) may be customized to correct eye conditions, such as spherical and chromatic aberration. By way of example, simulations with Lumerical Inc.'s™ FDTD (finite difference time domain) solver programs may be used to create phase profiles for spherical, cylindrical or multifocal platforms, which may reduce or avoid the need to produce costly prototypes before manufacture.

The deposition of TiO2 may result in an excess TiO2 layer on top of the resist. Thus, optionally, at block 810, the excess layer of TiO2 over the resist is etched away.

At block 812, the remaining resist is stripped. For example, the stripping may be performed using an overnight Remover-PG bath. The remaining TiO2 structures on the substrate form the metalens, which may achieve a refractive outcome that is equivalent or better than a conventional lens.

It is to be understood that the method of FIG. 8 is provided by way of example, and embodiments are not limited to this particular method of making a metalens.

Metalenses may be more efficient and have a higher numerical aperture than flat lenses made with diffractive optics because the wavelength scale ring structure of diffractive optics may degrade the phase profile of incident light. The sub-wavelength scale of nanofin phase disrupters of some metalenses have been shown to achieve excellent diffraction limited focus.

In addition to possibly reducing the size of ophthalmic devices, the metalens-based technology described herein may allow related tools to be reduced in size. For example, smaller phako tips, folders, cartridges and handpieces as well as enhancing laser cataract platforms (e.g. Femto Laser Assisted Cataract Surgery (FLACS)) for micro incisional surgery may be made for use together with the metalens-based IOL implants described herein.

Embodiments of the disclosure are not limited to the specific devices/implants shown in the drawings. Other ophthalmic devices, such as corneal inlays, may also incorporate one or more metalenses similar to the metalenses shown and described herein.

What has been described is merely illustrative of the application of the principles of the disclosure. Other arrangements and methods can be implemented by those skilled in the art without departing from the scope of the present disclosure.

The invention claimed is:

1. An ophthalmic device comprising:
a biocompatible polymer body; and
a planar metalens encapsulated within the polymer body, the metalens comprising:
a substantially transparent planar substrate having a first planar surface and a second planar surface opposite the first planar surface; and
a plurality of subwavelength structures dimensioned and arranged on the substrate in a pattern to focus visible light, the subwavelength structures comprising a dielectric material, wherein the device comprises an implant or inlay configured for implantation in an eye.

2. The ophthalmic device of claim 1, wherein the implant or inlay comprises one of: an intraocular lens implant; and an intracorneal lens inlay.

3. The ophthalmic device of claim 2, wherein the device comprises the intraocular lens implant, and the intraocular lens implant comprises one of: a phakic intraocular lens implant; and a posterior chamber intraocular lens implant.

4. The ophthalmic device of claim 1, wherein the dielectric material is titanium dioxide.

5. The ophthalmic device of claim 1, wherein the polymer body is hydrophobic.

6. The ophthalmic device of claim 5, wherein the polymer body comprises one of: acrylic polymer and silicone hydrogel.

7. The ophthalmic device of claim 1, wherein the plurality of subwavelength structures comprises nanopillars.

8. The ophthalmic device of claim 1, wherein the substrate comprises a polymer substrate.

9. The ophthalmic device of claim 8, wherein the polymer substrate is flexible.

10. The ophthalmic device of claim 9, wherein the polymer substrate comprises at least one of: silicone, acrylic and a hydrogel.

11. The ophthalmic device of claim 1, wherein the metalens is configured to correct an eyesight condition.

12. The ophthalmic device of claim 1, wherein the subwavelength structures each have at least one respective dimension that is less than a wavelength of the visible light.

13. The ophthalmic device of claim 12, wherein the at least one dimension comprises at least one of height, width and thickness of the subwavelength structure.

14. The ophthalmic device of claim 12, wherein the metalens interacts with the visible light over a range of visible light wavelengths.

15. A method for making an ophthalmic implant or inlay configured for implantation in an eye comprising:
providing a planar metalens comprising a substantially transparent and planar substrate and a plurality of subwavelength structures dimensioned and arranged on the substrate in a pattern to focus visible light, the substrate having a first planar surface and a second planar surface opposite the first planar surface, the subwavelength structures comprising a dielectric material; and
encapsulating the metalens in a biocompatible polymer body.

16. The method of claim 15, wherein providing the metalens comprises fabricating the metalens using an electron beam lithography (EBL) process.

17. The method of claim 15, wherein the dielectric material is titanium dioxide.

18. The ophthalmic device of claim 1, wherein the subwavelength structures are arranged on the first or second planar surface.

19. The method of claim 15, wherein the subwavelength structures are arranged on the first or second planar surface.

* * * * *